United States Patent
Chan et al.

(10) Patent No.: US 10,967,001 B2
(45) Date of Patent: *Apr. 6, 2021

(54) METHOD OF TREATING INFLAMMATION

(71) Applicant: CytoSorbents Corporation, Monmouth Junction, NJ (US)

(72) Inventors: Phillip P. Chan, Cherry Hill, NJ (US); Wei-Tai Young, Hillsborough, NJ (US); Vincent J. Capponi, Monmouth Junction, NJ (US); Thomas D. Golobish, Princeton, NJ (US); Humayra Begum Ali, Princeton Junction, NJ (US)

(73) Assignee: CYTOSORBENTS CORPORATION, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/018,603

(22) Filed: Jun. 26, 2018

(65) Prior Publication Data

US 2018/0311273 A1 Nov. 1, 2018

Related U.S. Application Data

(63) Continuation of application No. 15/635,517, filed on Jun. 28, 2017, now Pat. No. 10,034,894, which is a continuation of application No. 15/172,209, filed on Jun. 3, 2016, which is a continuation of application No. 13/637,775, filed as application No. PCT/US2011/030919 on Apr. 1, 2011, now Pat. No. 9,717,755.

(60) Provisional application No. 61/319,993, filed on Apr. 1, 2010.

(51) Int. Cl.
| | |
|---|---|
| *A61K 31/745* | (2006.01) |
| *A61K 31/74* | (2006.01) |
| *A61K 31/75* | (2006.01) |
| *A61K 9/00* | (2006.01) |
| *A61K 9/16* | (2006.01) |
| *A61K 9/50* | (2006.01) |
| *B01J 20/26* | (2006.01) |
| *B01J 20/28* | (2006.01) |
| *B01J 20/30* | (2006.01) |
| *C08F 212/36* | (2006.01) |
| *C08J 9/26* | (2006.01) |
| *A61K 47/58* | (2017.01) |

(52) U.S. Cl.
CPC .......... *A61K 31/745* (2013.01); *A61K 9/0053* (2013.01); *A61K 9/16* (2013.01); *A61K 9/50* (2013.01); *A61K 31/74* (2013.01); *A61K 31/75* (2013.01); *A61K 47/58* (2017.08); *B01J 20/261* (2013.01); *B01J 20/28004* (2013.01); *B01J 20/28073* (2013.01); *B01J 20/28076* (2013.01); *B01J 20/3064* (2013.01); *C08F 212/36* (2013.01); *C08J 9/26* (2013.01); *C08J 2201/0444* (2013.01); *C08J 2207/10* (2013.01); *C08J 2325/02* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,904,663 | A | 5/1999 | Braverman et al. |
| 6,416,487 | B1 | 7/2002 | Braverman et al. |
| 7,556,768 | B2 | 7/2009 | Brady et al. |
| 2006/0078534 | A1 | 4/2006 | Charmot et al. |
| 2006/0228416 | A1 | 10/2006 | Faure et al. |
| 2008/0119576 | A1 | 5/2008 | Young et al. |
| 2008/0138434 | A1 | 6/2008 | Brady et al. |
| 2010/0074954 | A1 | 3/2010 | Sonobe et al. |
| 2013/0011824 | A1 | 1/2013 | Chan et al. |
| 2013/0171206 | A1 | 7/2013 | Sonobe et al. |

FOREIGN PATENT DOCUMENTS

| | | |
|---|---|---|
| CA | 2771995 A1 | 4/2010 |
| CN | 101307149 | 11/2008 |
| EP | 1547605 | 6/2005 |
| EP | 1745792 | 1/2007 |
| WO | WO 94/26921 | 11/1994 |
| WO | WO 1999/034915 | 7/1999 |
| WO | WO 2003/057356 | 7/2003 |
| WO | WO 2006/044577 | 4/2006 |
| WO | WO 2007/132022 | 11/2007 |
| WO | WO 2010/040086 | 4/2010 |

OTHER PUBLICATIONS

De Vriese et al., "Cytokine removal during continuous hemofiltration in septic patients", J. Am. Soc. Nephrol., Apr. 1999, 10(4), 846-853.
European Patent Application No. 11763501.1: Extended European Search Report dated Nov. 27, 2013, 10 pages.
Gardiner et al., "Adsorbents as Anitendotoxiin Agents in Experimental Colitis", Gut, 1993, 34, 51-55.
International Patent Application No. PCT/US2011/030919: International Search Report and Written Opinion dated Jun. 13, 2011, 8 pages.
Peng et al., "Effects of Hemoadsorption on Cytokine Removal and Short-Term Survival in Septic Rats", Critical Care Medicine, May 1, 2008, 36(5), 1573-1577.
Valette et al., "Adsorption of low molecular weight proteins to hemodialysis membranes: experimental results and simulations", Biomaterials, Sep. 1999, 20(17), 1621-1634.

*Primary Examiner* — Robert A Wax
*Assistant Examiner* — Randeep Singh
(74) *Attorney, Agent, or Firm* — BakerHostetler

(57) ABSTRACT

The present invention concerns methods of treating systemic, regional, or local inflammation from a patient suffering or at risk of inflammation comprising administration of a therapeutically effective dose of a sorbent that sorbs an inflammatory mediator in said patient. In some preferred embodiments, the sorbent is a biocompatible organic polymer.

11 Claims, 4 Drawing Sheets

Figure 1

Adsorption of Botulinum Toxin A in PBS

Group 1 = top line, Group 2= middle line, Group 3 = bottom line.

METHOD OF TREATING INFLAMMATION

CROSS REFERENCE TO RELATED APPLICATIONS

This application is a continuation of U.S. patent application Ser. No. 15/635,517 (U.S. Published Application No. 2017-0296574), filed Jun. 28, 2017, which is a continuation of U.S. patent application Ser. No. 15/172,209 (U.S. Published Application No. 2016-0279163), filed Jun. 3, 2016, which is a continuation of U.S. patent application Ser. No. 13/637,775 filed on Mar. 8, 2013 (U.S. Pat. No. 9,717,755), issued Aug. 1, 2017, which is the National Stage of International Application No. PCT/US2011/030919, filed Apr. 1, 2011, which claims the benefit of U.S. Provisional Application No. 61/319,993, filed Apr. 1, 2010, the disclosures of each are incorporated herein by reference in their entireties.

TECHNICAL FIELD

The invention concerns, inter alia, methods of treating systemic, regional, or local inflammation from a patient suffering or at risk of such inflammation.

BACKGROUND

An inflammatory response occurs in animals when cells or tissues are injured by bacteria, trauma, toxins, heat, or other agents, which can be collectively referred to as "Inflammatory Agents." The nature and character of a given inflammatory response is regulated by the complex interaction of a variety of pro-inflammatory or anti-inflammatory stimulators or mediators, which are synthesized and released by cells and tissues. Some known species of pro-inflammatory or anti-inflammatory stimulators or mediators include cytokines, nitric oxide, thromboxanes, leukotrienes, phospholipids like platelet-activating factor, prostaglandins, kinins, complement factors, coagulation factors, superantigens, monokines, chemokines, interferons, free radicals, proteases, arachidonic acid metabolites, prostacyclins, beta endorphins, myocardial depressant factors, anandamide, 2-arachidonoylglycerol, tetrahydrobiopterin, cell fragments and chemicals including histamine, bradykinin, and serotonin. The discovery of new (i.e., previously unrecognized) species of pro-inflammatory or anti-inflammatory stimulators or mediators is an ongoing process.

The nature and intensity of inflammatory responses differ, depending on the site which has been invaded, and on the character of the Inflammatory Agent(s), and the interaction of pro-inflammatory or anti-inflammatory stimulators or mediators involved. The inflammatory response, when regulated and localized, is beneficial. If not regulated and generalized, however, the inflammatory response can cause significant tissue injury and even death.

Cytokines are one class of proteins produced predominantly by macrophages, monocytes, neutrophils and lymphocytes typically in response to a viral, bacterial, fungal or parasitic infection, as well as in response to T cell stimulation during an immune response. Cytokines are known to be synthesized by other cell types, such as stromal cells like fibroblasts, endothelial cells and smooth muscle cells, as well as epithelial cells, keratinocytes and hepatocytes. Cytokines are normally present in very low concentrations in the blood or tissues.

The structures and activities of cytokines have been the subject of many studies. It has become apparent that cytokines possess a wide spectrum of immunological and non-immunological activities. Cytokines affect diverse physiologic functions, such as cell growth, differentiation, homeostasis and pathological physiology. The art shows that cytokines have multiple biological activities and interact with more than one cell type. Cytokines are also known to be capable of stimulating their own synthesis, as well as the production of other cytokines from a variety of cell types. This phenomenon is called the "cytokine cascade." Cytokine cascades are often associated with systemic changes arising from infection and tissue injury and, in this context, they serve a myriad of biological functions. For example, various cytokines, categorized as the interleukins (IL), interferons (IF), and tumor necrosis factor (TNF), are produced during immune and inflammatory responses. These cytokines beneficially control various aspects of these responses. In this situation, the cytokine cascade mediates normal host defense responses, cell regulation, and cell differentiation.

Under cascade circumstances, the function of cytokine production can become disordered. This disorder can lead to the presence of larger than normal concentrations of cytokines. When the cytokine cascade becomes disordered, there can be a rapid extension and amplification of the intended localized host response in such a way that only one or a few initiating stimuli trigger the eventual release and participation of scores of host mediators. Although a number of features of the host response assist in fighting off invasion, an overly robust or poorly modulated endogenous response can rapidly accelerate to produce other profound alterations in host homeostasis at the cellular, tissue, and systemic levels. As a result, cytokine expression in a region of the body where tissues or organs are legitimately subject to bacterial infection or an immune response challenge, can, when disordered, lead to unwanted destruction of healthy tissue elsewhere in the body. Larger than normal concentrations of certain cytokines can cause disease and other deleterious health effects, some of which can be lethal.

A disordered cytokine cascade that leads to the increased presence of the cytokines IL-1 and TNF can, alone or in combination, cause a state in animals clinically identical to systemic inflammatory response syndrome (SIRS), sepsis, and more severe variants of sepsis called severe sepsis (sepsis with organ dysfunction) and septic shock (severe sepsis with refractory hypotension). These conditions can arise due to the individual, combined, and concerted effects of a large number of cytokines. Severe sepsis and septic shock afflicts more than 750,000 Americans every year. Cytokine-induced sepsis can be brought about by infection by a variety of microorganisms, including not only bacteria but also viruses, fungi, and parasites. SIRS or sepsis can also be initiated by host response to invasion in general, such as by cancer or as a result of major surgery or trauma. Septic shock is a potentially lethal cytokine-mediated clinical complication against which there is no generally effective therapeutic approach.

One of the best studied examples of cytokine-induced septic shock is the case of infection by gram-negative bacteria. The appearance of bacterial endotoxins, such as lipopolysaccharide (LPS), in the host bloodstream is believed to lead to the endogenous production of a variety of host factors that directly and indirectly mediate the toxicity of LPS. These host-derived mediators include many now well-recognized inflammatory cytokines, as well as endocrine hormones, in addition to a number of other endogenous factors such as leukotrienes and platelet activating factor. Among the interacting factors that together comprise the cytokine cascade, the cytokine TNF-alpha is believed to be the most important identified to date. During the ensuing cytokine cascade, the mediators that appear early in the invaded host are thought to trigger the release of later appearing factors. Many of the cytokine mediators not only exert direct functions at the targeted tissues, but also at other local and remote tissues, where subsequent responses to other mediators produced during the cascade occur, and so on. The result, if unchecked, can be a multifaceted pathological condition, which is characterized most prominently by deleterious hemodynamic changes, organ dysfunction and coagulopathy leading to multiple organ failure and, often, to death.

Multiple attempts have been made and still many others are currently underway to block specific mediators of this response. These attempts, however, have been relatively unsuccessful. Therapy aimed at single mediators cannot effectively attenuate the entire response. Furthermore, it is both the duration and intensity of inflammation that correlates best with outcome. Generally, higher concentrations of cytokines and longer duration of over-expression of proinflammatory cytokines are associated with higher mortality. Systemic inflammation results in organ injury which results in the prolongation of the inflammatory response and thus, more organ injury.

Similarly profound, but often less lethal, physiologic effects can occur as a result of abnormal production of certain cytokines, without the presence of exogenous bacterial toxins. As one example, cytokine TNF-alpha has been found to be an anti-tumor cytokine. As a result, TNF-alpha has been expected to be useful as an antitumor agent. However, it has been discovered that TNF-alpha is identical with cachectin, which is a cachexia-inducing factor. The disordered production of TNF-alpha has also been correlated with, not only severe sepsis and septic shock, but the incidence of rheumatoid arthritis, adult respiratory distress syndrome (ARDS), the severity of viral hepatitis, myocardial ischemia, and the inhibition of myocardial contraction. Also, TNF has recently been shown to be involved in initiating the expression of human immunodeficiency virus in human cells that carry latent virus, which could be a contributing factor in the expression of latent AIDS virus in certain individuals. Furthermore, a correlation between the TNF level in the blood and blood pressure has also been observed. As TNF levels increase, blood pressure decreases, which can lead to serious complications such as kidney failure. Hypotension and in severe cases, hemodynamic collapse or shock, can be caused by cytokines such as TNF through endothelial damage, leading to loss of fluid from the intravascular space to the surrounding tissues, as well as through TNF and other cytokine stimulation of inducible nitric oxide synthase, that leads to myocardial depression and peripheral vasodilation.

TNF-alpha has been observed to stimulate production of other types of cytokines, such as IL-1, etc. Cytokine IL-1 is known to be an important agent for inducing and transmitting the systemic biological response against infection and inflammation. IL-1 induces the usual, desirable responses observed in inflammation in general, such as fever, increase of leukocytes, activation of lymphocytes, and induction of biosynthesis of acute phase protein in liver. This cytokine is known to have a strong antitumor activity.

When IL-1 is produced in abnormally larger amounts, however, the result may contribute to the severity of chronic inflammatory diseases, such as rheumatoid arthritis. Thus, the abnormal activation of various cytokines such as the interleukins (IL) and tumor necrosis factor (TNF) is believed responsible for the tissue damage and pain that occurs in various inflammatory conditions like rheumatoid arthritis. In rheumatoid arthritis, levels of TNF, IL-1, IL-6 and IL-8 increase dramatically and can be detected in the synovial fluid. The cytokine cascade induced by expression of these cytokines results in depressed lipoprotein metabolism as well as bone and cartilage destruction.

As another example, the cytokine IL-6 plays an important role in antibody production in B cells. The cytokine IL-6 also is an important factor in body systems, e.g., the hematopoietic system, nervous system, and the liver, as well as in immune system. For example, IL-6 is effective for inducing proliferation and differentiation of T cells, inducing the production of protein at acute phase by acting on hepatic cells, and promoting the growth of cells in bone marrow.

A correlation between the abnormal secretion of IL-6 and various disease states (e.g., autoimmune diseases, such as hypergammaglobulinemia, chronic articular rheumatism, and systemic lupus erythematosus; the abnormal state of polyclonal B cells, as well as in the development of the abnormal state of monoclonal B cells such as myeloma cells; Castleman's disease accompanied with tumor of the lymph nodes, for which the cause is unknown; primary glomerular nephritis; and the growth of mesangial cells) has been observed.

As yet another example, in bacterial infections, cytokines such as IL-8 act as a signal that attracts white blood cells such as neutrophils to the region of cytokine expression. In general, the release of enzymes and superoxide anions by neutrophils is essential for destroying the infecting bacteria. However, if cytokine expression causes neutrophils to invade, for example, the lungs, release of neutrophil enzymes and superoxide anion can result in the development of adult respiratory distress syndrome (ARDS), which can be lethal.

Despite their diverse and myriad functions, most cytokines share one common feature. Although most cytokines are found in the size and molecular weight range of 8 to 80 kilodaltons, the majority of cytokines are within a narrow size and molecular weight range of 8 to 51 kilodaltons. This size characteristic is extremely important for the clearance of cytokines from the blood.

In disease states where the kidney has failed—which is often the case in septic shock—hemodialysis or hemofiltration membranes are used as substitutes for the glomerular membrane of the kidney. Artificial membranes, however, are severely limited in their ability to clear cytokines from the blood due to their inadequate porosity. In fact, the predominant mechanism by which these membranes remove cytokines in clinical practice is not filtration, but rather nonspecific surface adsorption (J. Am Soc Nephrol 1999 April; 10(4): 846-53, Cytokine removal during continuous hemofiltration in septic patients, De Vriese A S, Colardyn F A, Philippe J J, Vanholder R C, De Sutter J H, Lameire N H). Typically these membranes have 0.5 to 2 square meters of surface area available for adsorption that becomes saturated within the first 30 to 90 minutes of treatment (Biomaterials September 1999; 20(17):1621-34, Adsorption of low molecular weight proteins to hemodialysis membranes: experimental results and simulations, Valette P, Thomas M, Dejardin P). An improved external device taught in the art uses certain sorbent polymers to externally interact with blood to reduce levels of cytokines or other species of pro-inflammatory or anti-inflammatory stimulators or mediators in blood or physiologic fluids with significant specificity. See, U.S. Pat. Nos. 7,556,768; 6,416,487; and 5,904,663. While such methods are advantageous in treating certain inflammatory conditions, there is a need in the art for a simpler method that does not require use of an external removal device.

SUMMARY

In some aspects, the invention concerns methods of treating systemic, regional, or local inflammation from a patient suffering or at risk of inflammation comprising administration of a therapeutically effective dose of a sorbent for an inflammatory mediator (for example, a sorbent that sorbs the mediator) in the patient. In some methods, the inflammatory mediator is one or more of enzymes, cytokines, prostaglandins, eicosanoids, leukotrienes, kinins, complement, coagulation factors, toxins, endotoxins, enterotoxins, lipopolysaccharide, substances that induce apoptosis of cells, caustic substances, bile salts, fatty acids, phospholipids, oxidized byproducts, reactive oxygen species, oxygen radicals, surfactants, ions, irritant substances, cell fragments, interferon and immunomodulatory antibodies, biologics or drugs.

Certain inflammatory mediators are present in physiological fluid or a carrier fluid in the patient. Physiological fluids include nasopharyngeal, oral, esophageal, gastric, pancreatic, hepatic, pleural, pericardial, peritoneal, intestinal, prostatic, seminal, vaginal secretions, tears, saliva, mucus, bile, blood, lymph, plasma, serum, synovial fluid, cerebrospinal fluid, urine, and interstitial, intracellular, and extracellular fluid.

In some preferred methods, the dose of sorbent is administered orally, via a feeding tube, peritoneally, or rectally.

The inflammatory mediator may be associated with systemic inflammatory response syndrome (SIRS) or sepsis, such as from viral, bacterial, fungal or parasitic infection, autoimmune disease, surgery, cytotoxic chemotherapy, bone marrow manipulation, major tissue injury or trauma, mesenteric hypoperfusion, gut-mucosal injury, malaria, gastrointestinal inflammatory disease, enteric infection, influenza, acute lung inflammation such as acute respiratory distress syndrome or acute lung injury, pulmonary embolism, pancreatitis, autoimmune and collagen vascular diseases, transfusion-related diseases, burn injury, smoke or inhalation lung injury, graft versus host disease, ischemia or infarction, reperfusion injury, hemorrhage, anaphylaxis, drug overdose, radiation injury or chemical injury. In some embodiments, the inflammatory mediator results from a disease caused biowarfare pathogens, toxins or agents, such as viral hemorrhagic fevers, hantavirus cardiopulmonary syndrome (hantaviruses), cholera toxin, botulinum toxin, Ricin toxin, Q fever (*Coxiella burnetii*), Typhus (*Rickettsia prowaszekii*), or Psittacosis (*Chlamydia psittaci*).

In certain embodiments of the invention, the sorbent is a biocompatible polymer.

Some polymers can be supplied as a slurry, or suspension, or dry powder or other dry particulate capable of being wetted. In some methods, the sorbent is supplied as a slurry or suspension packaged in either single dose or multidose packages for oral administration. In other methods, the sorbent is supplied as a slurry or suspension packaged in either single dose or multidose packages for administration by enema or feeding tube or any combination therein.

The polymer can also be supplied as a dry powder or other dry particulate capable of being wetted externally or internally in the alimentary canal, including in the gastric or enteric environment, with or without the addition of wetting agents such as ethyl or isopropyl alcohol. In yet other embodiments, the polymer is supplied as tablet, dry powder, other dry particulate, capsule or suppository packaged in bottles or blister packs for administration.

In some methods, the polymer materials are not metabolizable by human and animal.

Some polymers comprise particles having a diameter in the range for 0.1 micron meters to 2 centimeters. Certain polymers are in the form of powder, beads or other regular or irregularly shaped particulate. The pore structure of some polymers is such that the total pore volume of pore size in the range of 50 Å to 3000 Å is greater than 0.5 cc/g to 3.0 cc/g dry polymer. In some embodiments, the polymer has a pore structure such that the total pore volume of pore size in the range of 50 Å to 3000 Å is greater than 0.5 cc/g to 3.0 cc/g dry polymer; wherein the ratio of pore volume between 50 Å to 3,000 Å (pore diameter) to pore volume between 500 Å to 3,000 Å (pore diameter) of the polymer is smaller than 200:1; and the ratio of pore volume between 50 Å to 3,000 Å (pore diameter) to pore volume between 1,000 Å to 3,000 Å (pore diameter) of the polymer is greater than 20:1.

In some embodiments, the polymer is a coated polymer comprising at least one crosslinking agent and at least one dispersing agent. The dispersing agents can be selected from such as hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly (dimethylaminoethyl acrylate), poly(diethylamimoethyl methacrylate), poly(diethylaminoethyl acrylate), poly(vinyl alcohol), poly(N-vinylpyrrolidinone), salts of poly(methacrylic acid), and salts of poly(acrylic acid) and mixtures thereof; the crosslinking agent selected from a group consisting of divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triiacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide and mixtures thereof; and the polymer is developed simultaneously with the formation of the coating, wherein the dispersing agent is chemically bound to the surface of the polymer.

Some preferred polymers comprise residues from one or more monomers selected from divnylbenzene and ethylvinylbezene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triiacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, divinylformamide and mixtures thereof.

Some suitable polymer include ion exchange polymers. In some embodiments, the polymer is a cellulosic polymer. In some embodiments, the polymers may be derivatized. Some polymers may be modified with an antibody or ligand. Such polymer may be porous or solid.

Certain preferred polymers are porous highly crosslinked styrene or divinylbenzene copolymer. In some embodiments, the porous highly crosslinked styrene or divinylbenzene copolymer is a macroporous or mesoporous styrene-divinylbenzene-ethylstyrene copolymer subjected to a partial chloromethylation to a chlorine content of up to 7% molecular weight. In certain embodiments, the porous highly crosslinked styrene or divinylbenzene copolymer is a hypercrosslinked polystyrene produced from crosslinked styrene copolymers by an extensive chloromethylation and a subsequent post-crosslinking by treating with a Friedel-Crafts catalyst in a swollen state. In other embodiments, the porous highly crosslinked styrene or divinylbenzene copolymer is a hypercrosslinked polystyrene produced from crosslinked styrene copolymers by an extensive additional post-crosslinking in a swollen state with bifunctional cross-linking agents selected from the group comprising of monochlorodimethyl ether and p-xylilene dichloride.

In another aspect of the invention, the polymer is a hydrophilic self wetting polymer that can be administered as dry powder or dry particulate containing hydrophilic functional groups such as chlorine, amines, hydroxyl, sulfonate, and carboxyl groups Certain polymers may be pyrolyzed.

The invention also concerns methods of preventing inhabitation of normal cell proliferation, activity, growth or regeneration comprising administration of a therapeutically effective dose of a sorbent to a patient that sorbs an inflammatory mediator in the patient. In some embodiments, the inhibition concerns cartilage and cartilage cells. In certain embodiments, the administration is accomplished by temporarily placing the sorbent in the joint or articular space.

BRIEF DESCRIPTION OF THE DRAWINGS

FIG. 1 shows a comparison of Botulinum Toxin A removal by porous polymer compared to non porous polymer and vehicle control.

DETAILED DESCRIPTION OF ILLUSTRATIVE EMBODIMENTS

Figure 2:
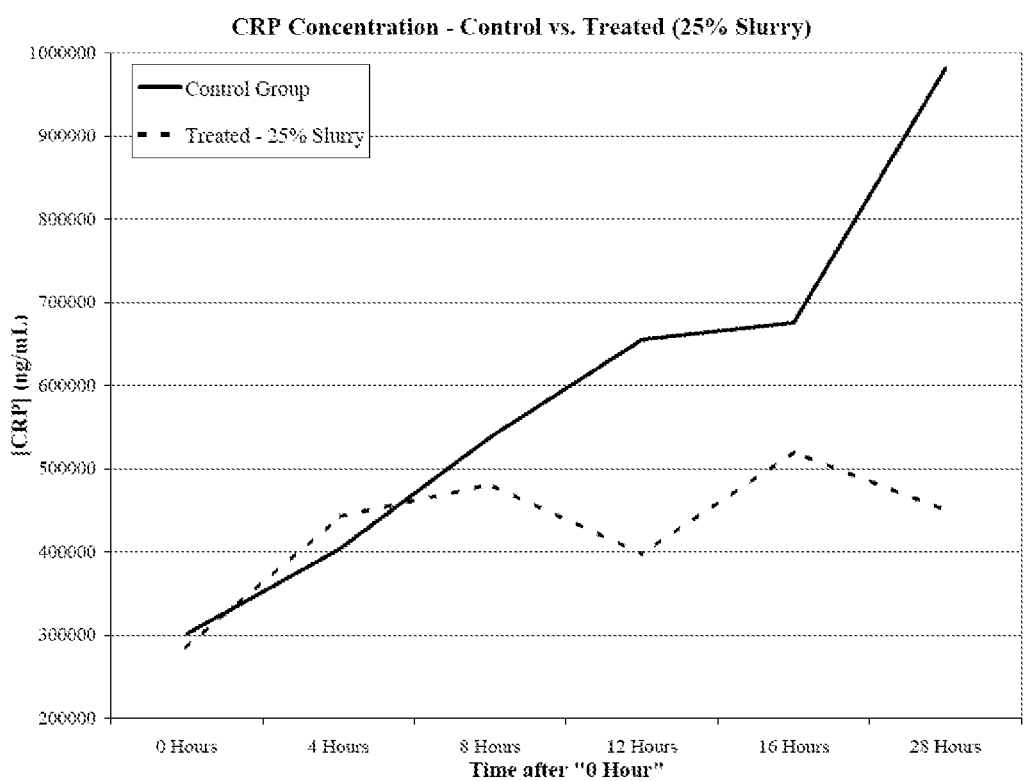
FIG. 2 presents a graph of C-reactive protein (CRP) concentration over time in animals with cecal ligation puncture induced infection and sepsis receiving an oral dose of a 25% slurry of porous beads in water compared to control water only.

In some aspects, the invention concerns methods of treating systemic, regional, or local inflammation from a patient suffering or at risk of inflammation by administering a therapeutically effective dose of a sorbent that sorbs an inflammatory mediator in the patient. An inflammatory mediator as we have defined it is any substance that can directly or indirectly elicit irritation, inflammation, injury or death of local or remote cells, tissues or organs. Inflammatory mediators include, but are not limited to, enzymes, cytokines, prostaglandins, eicosanoids, leukotrienes, kinins, complement, coagulation factors, toxins, endotoxins, enterotoxins, lipopolysaccharide, substances that induce apoptosis of cells including proteins such as Fas ligand, cell fragments, caustic substances such as acidic or basic secretions, bile salts, fatty acids, phospholipids, oxidized byproducts, reactive oxygen species, oxygen radicals, surfactants, ions, and irritant chemicals. Inflammatory mediators also include agents administered exogenously such as interferon and immunomodulatory antibodies, biologics or drugs. Indirect action could include, for instance, initiating a chain of events that leads to an activation of the pro-inflammatory immune response.

In some embodiments of the invention, the sorbent is used to sorb an inflammatory mediator present in physiological fluid or a carrier fluid in the patient. Physiologic fluids are liquids that originate from the body and can include, but are not limited to, nasopharyngeal, oral, esophageal, gastric, pancreatic, hepatic, pleural, pericardial, peritoneal, intestinal, prostatic, seminal, vaginal secretions, as well as tears, saliva, mucus, bile, blood, lymph, plasma, serum, synovial fluid, cerebrospinal fluid, urine, and interstitial, intracellular, and extracellular fluid, such as fluid that exudes from burns or wounds. Carrier fluids are exogenously administered liquids that include, but are not limited to, liquids administered orally, via a feeding tube, peritoneally, or rectally such as an enema or colonic wash.

The compositions of the present invention are useful in treating a wide variety of inflammatory conditions. For example, the methods can be used on conditions where the inflammatory mediator is associated with systemic inflammatory response syndrome (SIRS) or sepsis, caused by situations such as viral, bacterial, fungal or parasitic infections, autoimmune disease, surgery, cytotoxic chemotherapy, bone marrow manipulation, major tissue injury or trauma, mesenteric hypoperfusion, gut-mucosal injury, malaria, gastrointestinal inflammatory disease, enteric infection, influenza, acute lung inflammation such as acute respiratory distress syndrome or acute lung injury, pulmonary embolism, pancreatitis, autoimmune and collagen vascular diseases, transfusion-related diseases, burn injury, smoke and inhalation lung injury, graft versus host disease, ischemia or infarction, reperfusion injury, hemorrhage, anaphylaxis, drug overdose, radiation injury and chemical injury. The methods are also useful for treating conditions where a disease is caused specifically by potential biowarfare pathogens, toxins or agents including, but not limited to, anthrax (*Bacillus anthracis*), influenza, smallpox, SARS coronavirus, bubonic plague (*Yersinia pestis*), viral hemorrhagic fevers (filoviruses like Ebola and Marburg and arenaviruses like Lassa virus), tularemia (*Francisella tularensis*), hantavirus cardiopulmonary syndrome (hantaviruses), cholera toxin, botulinum toxin, Ricin toxin, Q fever (*Coxiella burnetii*), Typhus (*Rickettsia prowaszekii*), and Psittacosis (*Chlamydia psittaci*).

In addition to treatment of diseases or other inflammatory conditions or injuries, compositions disclosed herein may also be useful prophylactically for the prevention of such conditions.

Inflammatory mediators can inhibit normal cell proliferation, activity, growth or regeneration. Cartilage is one such example. It is generally believed that cytokines and inflammatory mediators and metalloproteinases (enzymes) are partly responsible for cartilage death in joints (rheumatoid arthritis, osteoarthritis, etc). Some believe that their presence in synovial fluid prevents cartilage and cartilage cells from being able to regenerate and regrow. By administering these polymers so as to place the sorbent (temporarily, in a preferred embodiment) in the joint or articular space (either in a contained or uncontained form) to sorb these mediators, cartilage and cartilage cells can be allowed to regrow in situ.

The compositions of the instant invention may be administered by methods well known to those skilled in the art. In some embodiments, administration is topical. Such methods include ophthalmic administration, administration to skin or wounds, direct administration into a body cavity or joint, and delivery to mucous membranes such as nasal, oral, vaginal and rectal delivery or other delivery to the alimentary canal. In some embodiments, such methods include local or systemic administration through an oral or parenteral route. In some embodiments, the treatment is extracorporeal. Extracorporeal administration would include removal of inflammatory mediators from blood or physiologic fluids by circulating the fluids through a device containing sorbent and returning it back to the body. Parenteral administration includes intravenous, intraarterial, subcutaneous, intraperitoneal or intramuscular injection or infusion; or intracranial (including intrathecal or intraventricular, administration).

Pharmaceutical compositions and formulations for topical administration include but are not limited to ointments, lotions, creams, transdermal patches, gels, drops, suppositories, sprays, liquids and powders. Utilization of conventional pharmaceutical carriers, oily bases, aqueous, powder, thickeners and the like may be used in the formulations.

The pharmaceutical compositions may also be administered in tablets, capsules, gel capsules, slurries, suspensions, and the like.

Penetration enhancers may also be used in the instant pharmaceutical compositions. Such enhancers include surfactants, fatty acids, bile salts, chelating agents, and non-chelating non-surfactants and are generally known in the art.

In some preferred embodiments, the administration of sorbent polymer is oral, or rectal, or via a feeding tube or any combination therein.

The polymers of the present invention can be administered once to a patient or in multiple doses.

Polymers useful in the invention may be supplied as a slurry, suspension or reconstituted from the dry state into a slurry or suspension. In some embodiments, the polymer may be supplied as a slurry or suspension packaged in either single dose or multidose bottles for oral administration. In other embodiments, the polymer may be supplied as a slurry or suspension packaged in either single dose or multidose bottles for administration by enema or feeding tube or any combination therein. In certain embodiments, the polymer is supplied as a dry powder capable of being wetted externally or in the alimentary canal with or without the addition of wetting agents such as ethyl alcohol.

The polymer may be supplied as tablet, capsule or suppository packaged in bottles or blister packs for administration. Depending on the use, the polymer may be sterile or non-sterile. The polymer may be sterilized by standard methods. Such methods are well known to those skilled in the art.

In some embodiments, the polymer materials used as the sorbent are substantially not metabolizable by human and animal. Certain polymers may be irregular or regular shaped particulates such as powders, beads, or other forms with a diameter in the range of 0.1 micron meters to 2 centimeters The polymers used in the instant invention preferably have a biocompatible and hemocompatible exterior surface coatings but are not absolutely necessary, especially in certain circumstances, such as oral or rectal administration. Certain of these coatings are covalently bound to the polymer particle (beads, for example) by free-radical grafting. The free-radical grafting may occur, for example, during the transformation of the monomer droplets into polymer beads. The dispersant coating and stabilizing the monomer droplets becomes covalently bound to the droplet surface as the monomers within the droplets polymerize and are converted into polymer. Biocompatible and hemocompatible exterior surface coatings can be covalently grafted onto the preformed polymer beads if the dispersant used in the suspension polymerization is not one that imparts biocompatibility or hemocompatibility. Grafting of biocompatible and hemocompatible coatings onto preformed polymer beads is carried out by activating free-radical initiators in the presence of either the monomers or low molecular weight oligomers of the polymers that impart biocompatibility or hemocompatibility to the surface coating.

By "biocompatible", it is meant that the polymer is capable of contact with living tissues or organisms without causing harm during the time that the polymer is in contact with the tissue or organism. In some embodiments, it is intended that the polymer is tolerated by the gut and alimentary canal of the organism. The polymers of the present invention are preferably non-toxic.

In one embodiment, the present invention relates to a porous polymer for sorbing small to midsize protein molecules and excluding sorption of large blood proteins, the polymer comprising a plurality of pores. The pores sorb small to midsize protein molecules equal to or less than 50,000 Daltons.

In some embodiments, the polymer has a preferential pore structure such that the total pore volume of pore size in the range of 50 Å to 3000 Å is greater than 0.5 cc/g to 3.0 cc/g dry polymer; wherein the ratio of pore volume between 50 Å to 3,000 Å (pore diameter) to the pore volume between 500 Å to 3,000 Å (pore diameter) of the polymer is smaller than 200:1; and the ratio of pore volume between 50 Å to 3,000 Å in diameter to the pore volume between 1,000 Å to 3,000 Å in diameter of the polymer is greater than 20:1. The said ratios can be alternatively specified in terms of pore surface area (such as the ratio of pore surface area between 50 Å to 3,000 Å to pore surface area between 500 Å to 3,000 Å of the polymer); and therefore is an alternative way of specifying the same pore structure.

Some preferred polymers are coated polymers comprising at least one crosslinking agent and at least one dispersing agent. Suitable dispersing agents include hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), poly(N-vinylpyrrolidinone), salts of poly(methacrylic acid), and salts of poly(acrylic acid) and mixtures thereof.

Suitable crosslinking agents include divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide and mixtures thereof. Preferably, the polymer is developed simultaneously with the formation of the coating, such that the dispersing agent gets chemically bound to the surface of the polymer.

Preferred polymers include those derived from one or more monomers selected from divnylbenzene and ethylvinylbezene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triiacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, divinylformamide and mixtures thereof.

Some preferred polymers are ion exchange polymers.

Some preferred polymers are cellulosic polymers. Suitable polymers include cross-linked dextran gels such as Sephadex®.

Certain preferred polymers are porous highly crosslinked styrene or divinylbenzene copolymer. Some of these polymers are a macroporous or mesoporous styrene-divinylbenzene-ethylstyrene copolymer subjected to a partial chloromethylation to a chlorine content of up to 7% molecular weight. Other of these polymers are a hypercrosslinked polystyrene produced from crosslinked styrene copolymers by an extensive chloromethylation and a subsequent post-crosslinking by treating with a Friedel-Crafts catalyst in a swollen state. Yet other of these polymers are a hypercrosslinked polystyrene produced from crosslinked styrene copolymers by an extensive additional post-crosslinking in a swollen state with bifunctional crosslinking agents selected from the group comprising of monochlorodimethyl ether and p-xylilene dichloride Some polymers useful in the practice of the invention are hydrophilic self wetting polymers that can be administered as dry powder containing hydrophilic functional groups such as, amines, hydroxyl, sulfonate, and carboxyl groups.

Certain polymers useful in the invention are macroporous polymers prepared from the polymerizable monomers of styrene, divinylbenzene, ethylvinylbenzene, and the acrylate and methacrylate monomers such as those listed below by manufacturer. Rohm and Haas Company, (now part of Dow Chemical Company): (i) macroporous polymeric sorbents such as Amberlite™ XAD-1, Amberlite™ XAD-2, Amberlite™ XAD-4, Amberlite™ XAD-7, Amberlite™ XAD-7HP, Amberlite™ XAD-8, Amberlite™ XAD-16, Amberlite™ XAD-16 HP, Amberlite™ XAD-18, Amberlite™ XAD-200, Amberlite™ XAD-1180, Amberlite™ XAD-2000, Amberlite™ XAD-2005, Amberlite™ XAD-2010, Amberlite™ XAD-761, and Amberlite™ XE-305, and chromatographic grade sorbents such as Amberchrom™ CG 71,s,m,c, Amberchrom™ CG 161,s,m,c, Amberchrom™ CG 300,s,m,c, and Amberchrom™ CG 1000,s,m,c. Dow Chemical Company: Dowex® Optipore™ L-493, Dowex® Optipore™ V-493, Dowex® Optipore™ V-502, Dowex® Optipore™ L-285, Dowex® Optipore™ L-323, and Dowex® Optipore™ V-503. Lanxess (formerly Bayer and Sybron): Lewatit® VPOC 1064 MD PH, Lewatit® VPOC 1163, Lewatit® OC EP 63, Lewatit® S 6328A, Lewatit® OC 1066, and Lewatit® 60/150 MIBK. Mitsubishi Chemical Corporation: Diaion® HP 10, Diaion® HP 20, Diaion® HP 21, Diaion® HP 30, Diaion® HP 40, Diaion® HP 50, Diaion® SP70, Diaion® SP 205, Diaion® SP 206, Diaion® SP 207, Diaion® SP 700, Diaion® SP 800, Diaion® SP 825, Diaion® SP 850, Diaion® SP 875, Diaion® HP 1MG, Diaion® HP 2MG, Diaion® CHP 55A, Diaion® CHP 55Y, Diaion® CHP 20A, Diaion® CHP 20Y, Diaion® CHP 2MGY, Diaion® CHP 20P, Diaion® HP 20SS, Diaion® SP 20SS, and Diaion® SP 207SS. Purolite Company: Purosorb™ AP 250 and Purosorb™ AP 400.

As used herein, the term "sorbent" includes adsorbents and absorbents.

As used herein, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The following examples are intended to be illustrative and not limiting.

Although not essential, a preferred embodiment would be a structure that was more selective for target compounds, such as an antibody or ligand-coated beads or powders that are either non porous or porous. In the case of porous beads combined with an antibody, the antibody would augment the broad removal properties of the porous polymer

EXPERIMENTAL

Example 1: Sorbent Syntheses

The synthesis process consists of (1) preparing the aqueous phase, (2) preparing the organic phase, (3) carrying out the suspension polymerization, and (4) purifying the resulting porous polymeric sorbent product. The aqueous phase compositions are the same for all the polymerizations. Table 1 Å lists the percentage composition of the aqueous phase and Table 1B gives the material charges typical for a five (5) liter-reactor polymerization run.

TABLE 1A

Aqueous Phase Composition

| | Wt. % |
|---|---|
| Ultrapure Water | 97.787 |
| Dispersing Agent: Polyvinylalcohol | 0.290 |
| Monosodium Phosphate | 0.300 |
| Disodium Phosphate | 1.000 |
| Trisodium Phosphate | 0.620 |
| Sodium Nitrite | 0.003 |

TABLE 1B

Material Charges for a Typical Five (5) Liter-Reactor Polymerization Run

| Volume of Aqueous Phase | 1750.00 ml |
|---|---|
| Density of Aqueous Phase | 1.035 g/ml |
| Weight of Aqueous Phase | 1811.25 g |
| Volumetric Ratio, Aqueous Phase/Organic Phase | 1.05 |
| Volume of Organic Phase | 1665.0 ml |
| Density of Organic Phase | 0.84093 g/ml |
| Weight of Organic Phase, Excluding Initiator Charge | 1400.15 g |
| Total Reaction Volume | 3415.0 ml |
| Total Reaction Weight | 3211.40 g |

Upon preparation of the aqueous phase and the organic phase, the aqueous phase is poured into the five-liter reactor and heated to 65° C. with agitation. The pre-mixed organic phase including the initiator is poured into the reactor onto the aqueous phase with the stirring speed set at the rpm for formation of the appropriate droplet size. The dispersion of organic droplets is heated to the temperature selected for the polymerization and is held at this temperature for the desired length of time to complete the conversion of the monomers into the crosslinked polymer and, thereby, set the pore structure. Unreacted initiator is destroyed by heating the bead slurry for two (2) hours at a temperature where the initiator half-life is one hour or less. For the initiator, benzoyl peroxide, the unreacted initiator is destroyed by heating the slurry at 95° C. for two (2) hours.

The slurry is cooled, the mother liquor is siphoned from the beads and the beads are washed five (5) times with ultrapure water. The beads are freed of porogen and other organic compounds by a thermal cleaning technique. This process results in a clean, dry porous sorbent in the form of spherical, porous polymer beads.

TABLE 1C

Components of Adsorbent Syntheses

| Porous Polymer Identity | Adsorbent 1 Wt. %[a] | Adsorbent 2 | Adsorbent 3 Wt. %[a] | Adsorbent 4 Wt. %[a] | Adsorbent 5 Wt. %[a] |
|---|---|---|---|---|---|
| Divinylbenzene, (DVB), Pure | 35.859 | Adsorbent 2 is a comercial resin, Amberlite XAD-16 ®, made by Rohm and Haas Company | 26.163 | 22.4127 | 22.4127 |
| Ethylvinylbenzene (EVB), Pure | 20.141 | | 14.695 | 12.5883 | 12.5883 |
| Inerts | 0.766 | | 0.559 | 0.4790 | 0.4790 |
| Toluene | 19.234 | | 27.263 | 64.521 | 54.841 |
| Isoctane | 24.00 | | 31.319 | 0.00 | 9.680 |
| Polymerizable Monomers | 56.00 | | 40.8584 | 35.00 | 35.00 |
| Porogen | 44.00 | | 59.1416 | 65.00 | 65.00 |
| Benzoyl Peroxide (BPO), Pure; Wt. % Based Upon Polymerizable Monomer Content | 1.03 | | 0.7447 | 2.00 | 4.00 |
| Polymerization, ° C./time, hrs. | 75°/10 hrs | | 80°/16 hrs | 70°/24 hrs 95°/2 hrs | 65°/24 hrs 95°/2 hrs |

[a]Wt. % Value is based upon the total weight of the organic phase excluding the initiator.

Example 2: Pore Structure Characterization

The pore structures of the sorbent polymer beds identified in TABLE 1C were analyzed with a Micromeritics ASAP 2010 instrument. The pore volume is divided up into categories within pore size ranges for each of the five sorbent polymers and these values are provided in TABLE 2. The Capacity Pore Volume is that pore volume that is accessible to protein sorption and consists of the pore volume in pores larger than 100 Å diameter. The Effective Pore Volume is that pore volume that is selectively accessible to proteins smaller than 35,000 Daltons and consists of pore diameters within the range of 100 to 250 Å diameter. The Oversized Pore Volume is the pore volume accessible to proteins larger than 35,000 Daltons and consists of the pore volume in pores larger than 250 Å diameter. The Undersize Pore Volume is the pore volume in pores smaller than 100 Å diameter and is not accessible to proteins larger than about 10,000 Daltons.

TABLE 2

| Porous Polymer Identity | Sorbent 1 | Sorbent 2 | Sorbent 3 | Sorbent 4 | Sorbent 5 |
|---|---|---|---|---|---|
| Pore Volume (cc/g) of pore diameter in the range 50 Å to 3,000 Å | 0.5512 | 1.509 | 1.711 | 0.67 | 0.89 |
| Pore Volume (cc/g) of pore diameter in the range 500 Å to 3,000 Å | 0.007 | 0.016 | 0.668 | 0.004 | 0.005 |
| Ratio of Pore Volume between 50 Å to 3,000 Å in diameter To Pore Volume between 500 Å to 3,000 Å in diameter | 84:1 | 95:1 | 3:1 | 183:1 | 170:1 |
| Pore Volume (cc/g) of pore diameter in the range 1,000 Å to 3,000 Å | 0.002 | 0.006 | 0.010 | 0.001 | 0.002 |
| Ratio of Pore Volume between 50 Å to 3,000 Å in diameter To Pore Volume between 1,000 Å to 3,000 Å in diameter | 264:1 | 241:1 | 165:1 | 900:1 | 497:1 |
| % Cytochrome-C, Sorbed | 89% | 97% | 95% | 57% | 90% |
| % Albumin Sorbed | 4% | 8% | 13% | 1.0% | 1.8% |
| Selectivity | 24.05 | 11.94 | 7.27 | 57.1 | 50.06 |
| Pore Volume (cc/g) of pore diameter in the range 100 to 3,000 Å | 0.573 | 1.214 | 1.555 | 0.264 | 0.67 |
| Pore Volume (cc/g) of pore diameter in the range 200 to 3,000 Å | 0.211 | 0.711 | 1.345 | 0.012 | 0.02 |
| Pore Volume (cc/g) of pore diameter in the range 300 to 3,000 Å | 0.013 | 0.031 | 1.169 | 0.007 | 0.01 |

Example 3: Administration of a Sorbent to a Patient Exposed to an Unknown Pathogen A person is exposed to an unknown pathogen or toxin during an epidemic or bioterrorism attack. The mode of exposure is through one of many different means such as food or water ingestion, aerosol inhalation or skin contact. The pathogen is one of many such as *Bacillus anthracis* (anthrax), influenza virus, smallpox virus, *Yersinia pestis* (plague), Ebola or Marburg virus, *Francisella tularensis* (tularemia), hantavirus, cholera toxin, botulinum toxin, ricin toxin, *Salmonella, Escherichia coli* such as *E. coli* O157:H7, *Shigella, Listeria*, or others. Although the organism is not yet identified, other people are rapidly becoming seriously ill with similar symptoms, including high fever, rigors, cough, severe fatigue, and diarrhea. The patient may receive standard of care therapy such as antivirals, antibiotics, antitoxins, immunoglobulins. Then, as a prophylactic measure or to treat a patient who is developing symptoms of the infection and signs of inflammation (fever, chills, etc), the patient is orally administered milligram to gram quantities of a slurry or suspension of the sorbent polymer particulate or a tablet or capsule containing the sorbent polymer. Once distributed in the alimentary canal, particularly to the intestines, the sorbent captures, binds and sequesters inflammatory mediators exogenously introduced, or locally produced, or being introduced to the alimentary canal through physiologic fluids such as bile, before these inflammatory mediators can induce further inflammation, or toxicity, or cause a degradation of the intestinal lining that can lead to worsened inflammation, infection, endotoxemia and sepsis. By removing these inflammatory mediators, the sorbent polymer reduces the triggers for additional systemic inflammation in the patient, reducing systemic inflammatory mediator production, such as cytokines, thereby preventing or limiting the development of cytokine or other inflammatory mediator-induced cell death, organ damage, multi-organ failure and potentially death. The sorbent is administered once or repeatedly over the course of many hours to days to have a durable or persistent effect. The patient continues to receive antimicrobial therapy. The sorbent is then excreted and eliminated from the patient's system, without being metabolized or degraded or otherwise retained in the body. The sorbent prevents the patient from developing severe sepsis, septic shock, or serious organ dysfunction.

Example 4: Administration of a Sorbent to a Patient with Inflammatory Bowel Disease A patient with inflammatory bowel disease develops an exacerbation with constant severe diarrhea. The patient is administered standard of care therapy which may include systemic steroids and parenteral anti-TNF therapy. As part of the patients oral and rectal topical anti-inflammatory regimen, the patient is administered an oral suspension of the sorbent polymer as well as an enema containing the sorbent polymer. The sorbent binds, sequesters and removes locally produced inflammatory mediators, including cytokines, that are being produced enterally, and facilitates elimination of these mediators through excretion of the sorbent. This promotes healing of the intestine and a remission of the flare.

Example 5: Administration of a Sorbent to a Burn Patient

A burn patient suffers severe full thickness burns over 30% of his total body surface area as well as prolonged smoke and chemical inhalation lung injury. Despite debridement of the burns, the patient develops a severe systemic inflammatory response syndrome with the onset of acute respiratory distress syndrome requiring mechanical ventilation. The patient is administered the standard of care, which involves mainly supportive care measures. To counter the systemic inflammation that is leading rapidly to multi-organ failure, the patient is administered the sorbent polymer. Because the patient is unconscious, a feeding tube is used to deliver a slurry of the sorbent polymer to the alimentary canal to protect the intestinal lining from inflammatory mediators and to limit systemic inflammation. The patient's blood can then be treated extracorporeally by using a standard hemodialysis machine to pump the blood through a highly hemocompatible version of the sorbent, which is capable of removing systemic inflammatory mediators that can lead to the production of more inflammatory mediators. Treatment with the sorbent occurs over many days until the systemic inflammation subsides and injured organs, including the lungs, begin to heal and recover.

Example 6: In Vitro Botulinum Neurotoxin A1 Binding Study—Protocol Summary

Figure 1:
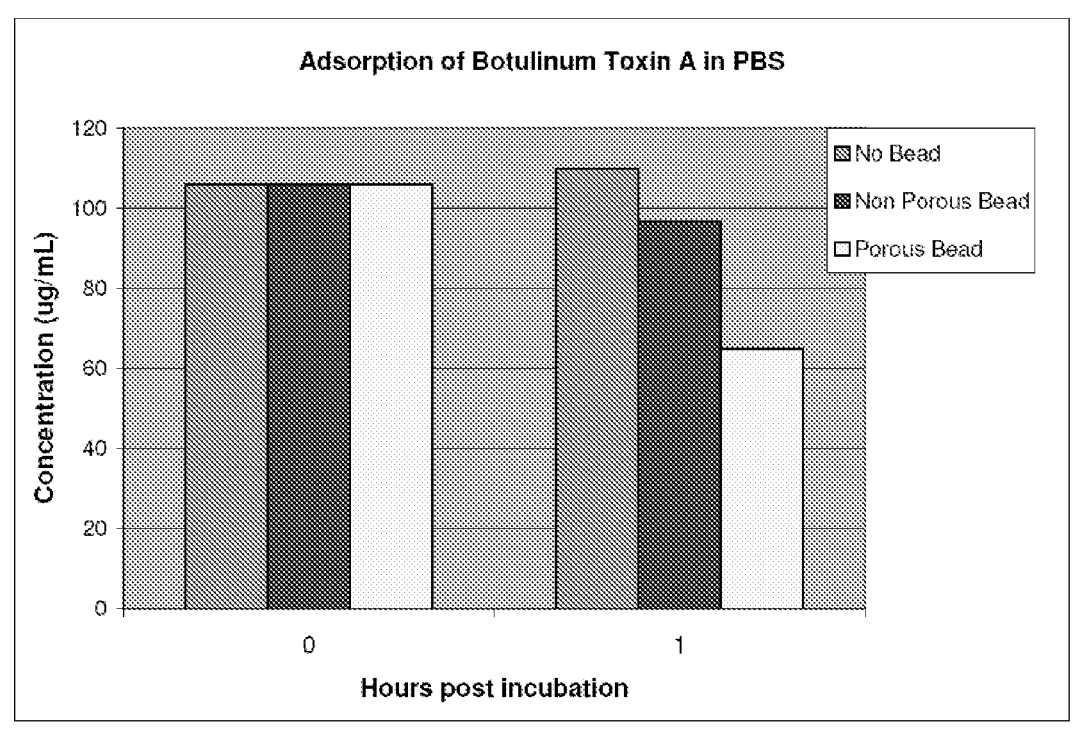

This study evaluates the ability of CytoSorbents' porous polymer beads to bind and clear Botulinum Neurotoxin Type A1 (BoNT/A1) from Phosphate Buffered Saline (PBS). The beads used in this study are representative of the polymers described in this patent application. Divinylbenzene polymer porous test beads and non-porous test beads were suspended in sterile PBS (pH 7.4). A stock solution of BoNT/A1 in PBS was prepared at a concentration of 100 ug/mL (Tufts). Two (2) mL of a PBS solution containing 100 ug/mL of BoNT/A1 (Tufts, Boston Mass.) was incubated in sterile, wide-mouth 5 mL conical tubes (Stockwell #3206; 5 tubes/bead type) containing either no beads, 100 uL dewetted non-porous beads, or 100 uL dewetted porous beads (TDG-057-118-SS). The extrabead volume was nominal in each case. 0.5 uL of the stock solution was removed and stored on ice (4° C.) for future analysis (T=0). Tubes were sealed and gently agitated for 60 minutes at room temperature. The beads were allowed to settle and 0.5 mL samples of the supernatant were also placed on ice. Samples were evaluated for BoNT/A1 concentration via standard BCA (bicinchoninic acid) Protein Assay. The results demonstrate the relative impact of no bead, non-porous beads and porous beads in BoNT/A1 removal. Porous beads reduced BoNT/A1 by 38.8% in this assay, compared to an 8.6% removal by non-porous beads and a 3.9% increase in the no bead control. Results are presented in FIG. 1.

TABLE 2

| | BoNT/A1 removal by bead type. | | |
|---|---|---|---|
| Time (hr) | No Bead | Non-Porous | Porous |
| 0 | 105.8 | 105.8 | 105.8 |
| 1 | 109.94 | 96.69 | 64.78 |

Example 7: Protocol Summary for Oral Administration of Porous Polymer Beads in a Cecal Ligation Puncture Sepsis Rat Model This example investigates the therapeutic effect of a 25% oral dose, by volume, of porous polymer beads on 19 week old Sprague-Dawley rats that had undergone cecal ligation puncture (CLP) causing polymicrobial sepsis. The beads used in this study are representative of the polymers described in this patent application.

Grouped in four cohorts of 8 animals (4 control and 4 treated), 32 rats were acclimated for a minimum of three days prior to the start of the study; those that appear to be in obvious poor health were not be used in the study. Animals were fasted for 16 hours before the surgical procedure was performed. Animals received subcutaneous injections of Buprenorphine 0.1 mg/kg prior to surgery and then at 6-12 hour intervals post-surgery. All surgeries were performed using short acting isoflourane to minimize the deleterious effects of anesthesia on cardiovascular functions. The surgical procedure involved a 5 cm midline laparotomy beginning 2 cm below the sternum. The cecum was isolated outside of the abdominal cavity on sterile gauze to avoid blood vessel damage. The cecum was then ligated with 2-0 Vicryl just below the ileocecal valve, maintaining bowel continuity. The cecal contents were then milked to one end of the cecum. The cecum was punctured 3 times with a 20-gauge needle, and then manipulated to extrude a single droplet of fecal material from each puncture site. The abdominal cavity was then closed in two layers, followed by fluid resuscitation and the animal returned to the appropriate cage.

Animals were checked 2 hours post-surgery, prior to the end of the day, and first-thing the next morning. The rats were allowed food and water ad libitum. Approximately 20 hours post-surgery, living animals were orally-dosed with 4 mL of either distilled water (N=8 for the control group) or 25% polymer slurry in distilled water (N=14) using a sterile disposable gavage feeding tube. 12 hours later, the animals were orally dosed an additional 4 mL of 25% polymer slurry. Animals that died before 20 hours post-CLP and before the first treatment dose were excluded from the study.

Detailed clinical observations were made and recorded on the day of surgery and on the day of dosing. Animals were observed for clinical signs once daily after dosing. Assessment included, but was not limited to, activity, posture, respiration, hydration status, and overall body condition.

Euthanasia was performed via inhalation of isoflourane or carbon dioxide gas followed by cervical dislocation. Euthanized animals underwent a gross necropsy and were discarded. Euthanasia was conducted in accordance with accepted American Veterinary Medical Association guidelines.

Prior to the first dosing, all animals demonstrated signs of a systemic inflammatory response, with cold paws, fur raising, hunched posture, inactivity and other clinical indicators of sepsis. Post-mortem gross pathology demonstrated erythema, edema and many surgical adhesions in the peritoneal cavity amongst animals that died, while surviving animals had markedly less pathology.

CRP Concentration—Control Vs. Treated (25% Slurry)

Effect of an Oral Dose of Porous Polymer on C-reactive protein (CRP) concentration over time. 16 Sprague Dawley rats were initially randomized into each group (control and treated) and underwent cecal ligation puncture (CLP) surgery in four separate cohorts of 4 control animals and 4 treatment animals. Animals that died in the pre-dosage period (<20 hours post-surgery) were excluded from these data. At 20 and 32 hours after CLP, animals were gavaged with either 4 mL water (control) or 4 mL of a 25% slurry of porous beads in water. The "0 Hours" time point on the graph is equivalent to 20 hours post-surgery. CRP Concentrations (ng/mL) were determined from plasma samples taken at time points of 0, 4, 8, 12, 16, and 28 hours beyond the "0 Hours" time point in surviving animals. Results are presented in FIG. 2. The control group results are represented by the solid line (n=8) and the treated group results are represented by the dashed line (n=14). CRP is a general marker of systemic inflammation.

Percent of Animals Living Vs. Time

Figure 3:
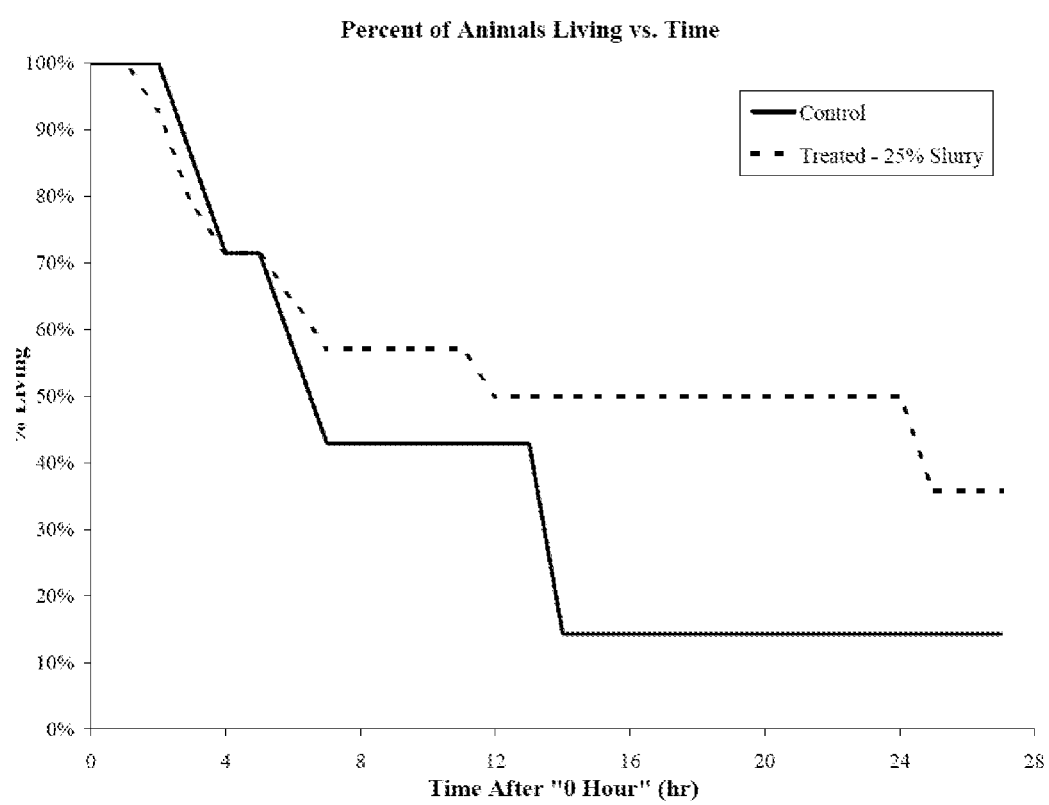
FIG. 3 shows percent of animals with cecal ligation puncture induced infection and sepsis that are living versus time after oral administration of porous polymer.

Effect of an Oral Dose of Porous Polymer on Survival. 16 Sprague Dawley rats were initially randomized into each group (control and treated) and underwent cecal ligation puncture (CLP) surgery in four separate cohorts of 4 control animals and 4 treatment animals. Animals that died in the pre-dosage period (<20 hours post-surgery) were excluded from these data. At 20 and 32 hours after CLP, animals were gavaged with either 4 mL water (control) or 4 mL of a 25% slurry of porous beads in water. The "0 Hours" time point on the FIG. 3 is equivalent to 20 hours post-surgery. Survival time was observed from the "0 Hour" time point up to 27 hrs. At 28 hours all animals were sacrificed. The Control group results are represented by the solid line (n=7) and the Treated group results are represented by the dashed line (n=14).

Example 8: Evaluation of Therapeutic Activity of an Orally Administered Porous Polymer Bead Slurry in the TNBS Colitis Model in Mice—Protocol Summary This example evaluates the therapeutic activity of an orally administered porous polymer bead slurry at two different doses administered twice a day in the TNBS (2,4,6-trinitrobenzenesulfonic acid) colitis model in mice. The beads used in this study are representative of the polymers described in this patent application.

The health status of the animals used in this study was examined on arrival. Only animals in good health were acclimatized to laboratory conditions and were used in the study. Animals were provided ad libitum with a commercial sterile rodent diet and had free access to sterile drinking water that was supplied to each cage via polyethylene bottles with stainless steel sipper tubes. Table 3 lists the experimental groups that comprised the study.

TABLE 3

| | | | Experimental Groups | | | | |
|---|---|---|---|---|---|---|---|
| Group | Group Size | Test Item | Done | Volume | Route | Dose Regime | TNBS Induction |
| 1 | N = 16 | Vehicle (DW) | 0.150 ml DW* | 5 ml/kg | PO | Twice a day starting on | TNBS in 40% |
| 2 | N = 16 | TDG-057-145 Modified, Batch | 0.150 ml* (50% | 5 ml/kg | PO | study day 0, 10 hours post | ethanol on study day 0 |

TABLE 3-continued

Experimental Groups

| Group | Group Size | Test Item | Done | Volume | Route | Dose Regime | TNBS Induction |
|---|---|---|---|---|---|---|---|
| | | 1, −106/+45 50% | compound suspended in water) | | | TNBS induction and through the end of the study* | |
| 3 | N = 4 | Sham | 0.150 ml DW* | 5 ml/kg | PO | Twice a day starting on study day 0 | 40% ethanol on study day 0 |

*NOTE:
Immediately after Group 2 dosed with 0.150 ml of TI, an additional of 0.150 ml of water was drawn into the same syringe used to gavage the animals and administered. This 2$^{nd}$ step washed down any residual compound in the syringe to assure maximum dose delivery Groups 1 and 3 were dosed with 0.150 ml of DW and followed by an additional 0.150 ml of DW which was drawn into the same syringe used to gavage the animals and administered.

Animals from Groups 1-3 were induced with 80 μL (0.8 mL) TNBS dissolved in 80% ethanol at 1:1 ratio (final ethanol concentration=40%) into the colon, 4 cm proximal to the anus through the rectum. The animals were kept in a vertical position for 60 seconds before being returned to their cages. Animals from group 3 were only given 40% ethanol as a negative control of the induced groups.

All TI dosing solutions were applied twice daily on each of the repeated dosing sessions starting on Study Day 0, 10 hours post-TNBS induction and through the end of the study (Day 7). For the control animals in groups 1 and 3, only water was be gavaged in place of TI dosing.

Prior to gavage feeding, the following procedures were performed:
1) The samples were rocked/swirled to evenly suspend the polymer while avoiding entraining air.
2) The syringes were primed once with water to fill all void spaces in the syringe needle and barrel and water was expelled to remove air bubbles. The mouse was gavaged IMMEDIATELY to prevent Test Item settling.
3) Between animals, samples were gently mixed to ensure a homogeneous suspension. If there was a delay in gavaging the animal after drawing up the polymer slurry, the contents in the syringe were mixed by inverting the syringe several times to ensure homogeneity.
4) After the animal was dosed with 0.150 mL of TI, an additional 0.150 mL of water was drawn into the same syringe to gavage the animal. This step assured the maximum dose delivery.
5) When not in use, the polymer slurries were stored in a refrigerator.

Throughout the entire 8-day duration of the study, careful clinical examinations of the animals were carried out in a blinded fashion and recorded once daily. Observations included changes in skin, fur, eyes, mucous membranes, occurrence of secretions and excretions (e.g. diarrhea) and autonomic activity (e.g. lacrimation, salivation, piloerection, pupil size, unusual respiratory pattern). Changes in gait, posture and response to handling, as well as the presence of unusual behavior, tremors, convulsions, sleep and coma were also noted.

Individual body weights of each animal were measured on Study Day 0 (Study Commencement) and on a daily basis thereafter through study termination (Study Day 7). NOTE: If an animal died or was euthanized during the study, its last weight was kept constant for the remaining days. This method allowed some representation of this animal throughout the study.

Body weight, stool consistency and bleeding per rectum, as well as any abnormalities observed in fur coat and abdomen were recorded daily. Total clinical score was presented as a SUM of all the parameters listed in the Table 4.

TABLE 4

Total Clinical Scores

| Weight Loss % | Score | Stool Consistency | Score | Fur Coat* | Score | Abdomen* | Score |
|---|---|---|---|---|---|---|---|
| None | 0 | Normal | 0 | None | 0 | None | 0 |
| 1-5 | 1 | Redness, swelling of the anus | 1 | Fur | 1 | Abdomen | 1 |
| 5-10 | 2 | Loose stool | 2 | Fur | 1 | Abdomen | 1 |
| 10-15 | 3 | Diarrhea | 3 | Fur | 1 | Abdomen | 1 |
| >15 | 4 | Diarrhea + Blood | 4 | Fur | 1 | Abdomen | 1 |
| Death | 11 | — | — | — | — | — | — |

*NOTE:
Abnormalities in fur coat and abdomen included but were not limited to: shaggy fur and swollen abdomen.

All living animals were euthanized at the end of the study.

Animals found in a moribund condition and/or animals showing severe pain and enduring signs of severe distress were humanely euthanized. In addition, and unless decided otherwise in the course of the study, animals that showed a decrease of body weight greater than 20% from initial body weight determination were humanely euthanized in accordance with animal regulations. All such events were recorded in the final report.

Figure 4:
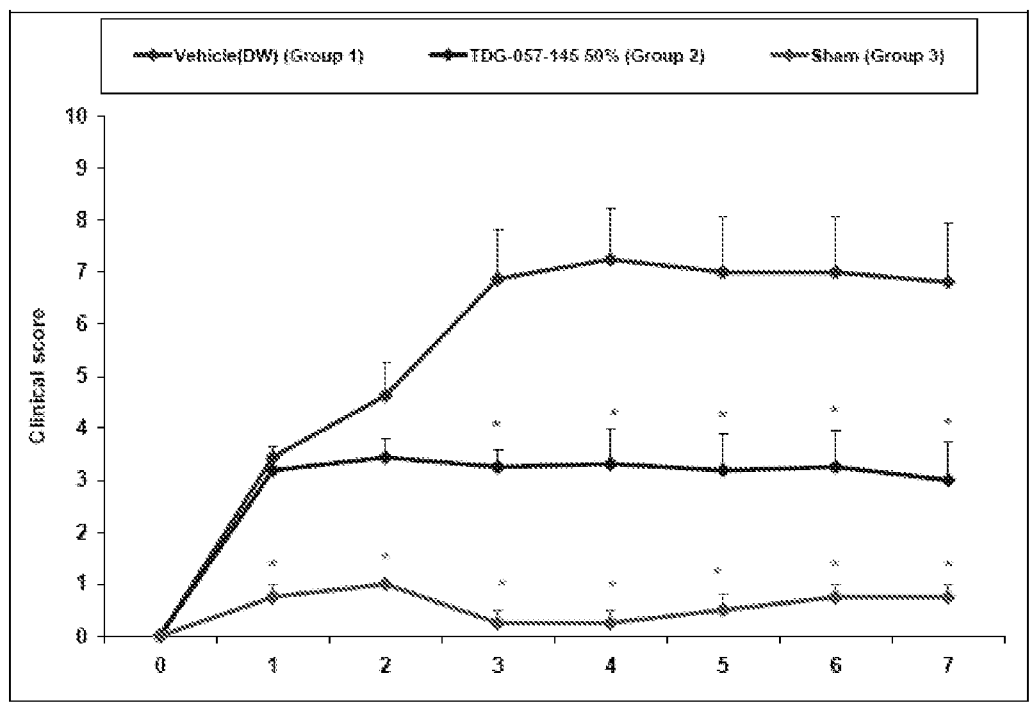
FIG. 4 presents a comparison mean clinical score for control vs treatment for TNBS Colitis model.

Results from the blinded evaluation are presented in FIG. 4.

What is claimed:

1. A method of treating systemic, regional, or local inflammation in a patient, said method comprising administration of a therapeutically effective dose of a sorbent for an inflammatory mediator in said patient; wherein the sorbent is a biocompatible polymer;
the biocompatible polymer comprising residues from one or more monomers selected from divinylbenzene, ethylvinylbezene, styrene, ethylstyrene, and mixtures thereof,
the biocompatible polymer having a pore structure such that the total pore volume of pore size in the range of 50 Å to 3000 Å is greater than 0.5 cc/g to 3.0 cc/g dry polymer; wherein the ratio of pore volume between 50 Å to 3,000 Å (pore diameter) to the pore volume between 500 Å to 3,000 Å (pore diameter) of the polymer is smaller than 200:1; or the ratio of pore volume between 50 Å to 3,000 Å in diameter to the pore volume between 1,000 Å to 3,000 Å in diameter of the polymer is greater than 20:1, said sorbent being administered orally, via a feeding tube, peritoneally, or rectally;

wherein said inflammatory mediator is a cytokine produced in response to an infection in said patient chosen from endotoxemia, *Bacillus anthracis* (anthrax), influenza virus, smallpox virus, *Yersinia pestis* (plague), Ebola virus, Marburg virus, *Francisella tularensis* (tularemia), hantavirus, cholera toxin, botulinum toxin, ricin toxin, *Salmonella, Escherichia coli, Shigella*, or *Listeria*.

2. The method of claim 1, wherein the biocompatible polymer comprises cross-linked, porous styrene or divinylbenzene copolymer.

3. The method of claim 1, wherein said inflammatory mediator is present in physiological fluid or a carrier fluid in the patient.

4. The method of claim 3, wherein said physiological fluids is nasopharyngeal, oral, esophageal, gastric, pancreatic, hepatic, pleural, pericardial, peritoneal, intestinal, prostatic, seminal, vaginal secretions, tears, saliva, mucus, bile, blood, lymph, plasma, serum, synovial fluid, cerebrospinal fluid, urine, and interstitial, intracellular, or extracellular fluid.

5. The method of claim 1, wherein said biocompatible polymer comprises particles having a diameter in the range for 0.1 micron meters to 2 centimeters.

6. The method of claim 1, wherein said biocompatible polymer is in the form of powder or beads.

7. The method of claim 1, wherein the sorbent is supplied as slurry, or suspension, or dry powder.

8. The method of claim 1, wherein said biocompatible polymer is a coated polymer comprising at least one cross-linking agent and at least one dispersing agent;

said dispersing agents such as hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), poly(N-vinylpyrrolidinone), salts of poly(methacrylic acid), and salts of poly(acrylic acid) and mixtures thereof;

said crosslinking agent selected from a group consisting of divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triiacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide and mixtures thereof;

wherein said dispersing agent is chemically bound to said surface of said biocompatible polymer.

9. The method of claim 1, wherein the cytokine is produced in response to an infection in said patient from *E. coli* 0157:H7.

10. The method of claim 1, wherein the cytokine is produced in response to an infection in said patient from *Bacillus anthracis* (anthrax), influenza virus, smallpox virus, *Yersinia pestis* (plague), cholera toxin, botulinum toxin, ricin toxin, *Salmonella, Escherichia coli, Shigella*, or *Listeria*.

11. The method of claim 1, wherein the cytokine is produced in response to an infection in said patient from endotoxemia, Ebola virus, Marburg virus, *Francisella tularensis* (tularemia), or hantavirus.

\* \* \* \* \*